United States Patent [19]

Scott et al.

[11] Patent Number: 4,906,788

[45] Date of Patent: Mar. 6, 1990

[54] COMBINED DEHYDROGENATION ETHERIFICATION PROCESS

[75] Inventors: Norman H. Scott, Arlington Heights; Bipin V. Vora, Darien, both of Ill.

[73] Assignee: UOP, Des Plaines, Ill.

[21] Appl. No.: 262,928

[22] Filed: Oct. 26, 1988

Related U.S. Application Data

[63] Continuation-in-part of Ser. No. 68,502, Jul. 1, 1987, abandoned.

[51] Int. Cl.$^4$ .............................................. C07C 41/06
[52] U.S. Cl. ................................... 568/697; 568/699; 585/315
[58] Field of Search ................ 568/697, 699; 585/315

[56] References Cited

U.S. PATENT DOCUMENTS

| | | | |
|---|---|---|---|
| 4,219,678 | 8/1980 | Obenaus et al. ..................... | 568/697 |
| 4,447,653 | 5/1984 | Vora .................................... | 568/697 |
| 4,465,870 | 8/1984 | Herskovitz ........................... | 568/697 |

*Primary Examiner*—Howard T. Mars

*Attorney, Agent, or Firm*—Thomas K. McBride; John G. Tolomei

[57] ABSTRACT

A combined process for the dehydrogenation of $C_4$-$C_5$ paraffins in a first zone and the etherification of olefins in a second zone improves efficiency by directly charging all but the lightest components of the dehydrogenation zone effluent to the etherification zone. This process is particularly suited for the production of gasoline boiling range ethers where an isoparaffin is dehydrogenated in a first zone to produce isoolefins. After separation of hydrogen and methane, the dehydrogenation zone effluent is charged along with methanol to an etherification zone for the production of MTBE. The etherification zone effluent is separated into at least three component streams comprising light ends, isoparaffins, and the ether product. Isoparaffins, separated from the etherification zone effluent, are recycled and combined with the feed to dehydrogenation zone. The particular arrangement of this invention uses an etherification zone for the production of MTBE and a single fractionation column to yield an overhead stream of light ends, a sidecut stream of recycle isoparaffins and methanol, and a bottoms product stream of MTBE.

11 Claims, 1 Drawing Sheet

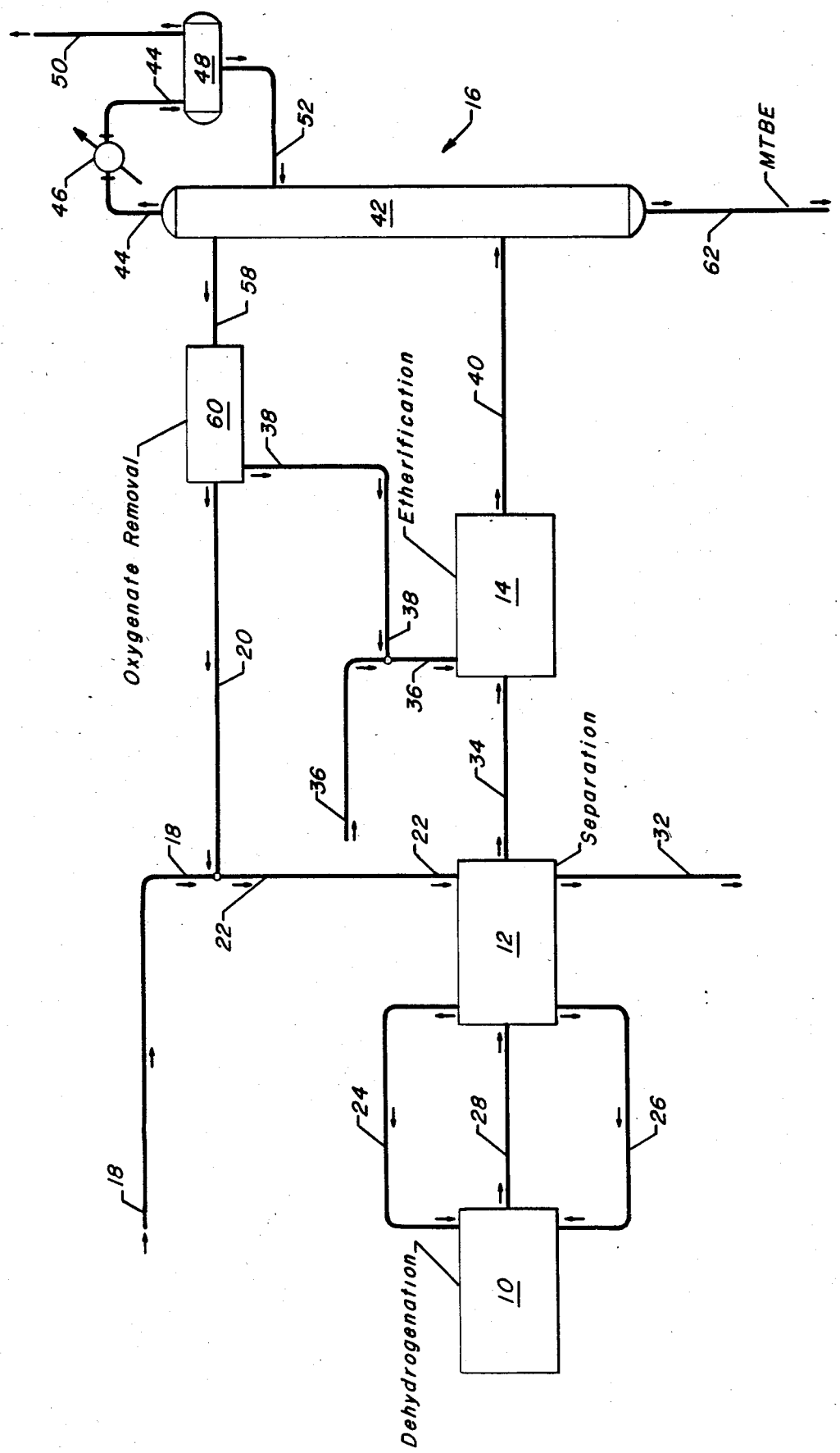

COMBINED DEHYDROGENATION ETHERIFICATION PROCESS

CROSS-REFERENCE TO RELATED APPLICATIONS

This application is a continuation-in-part of pending application Ser. No. 068,502, filed July 1, 1987, and now abandoned, the contents of which are incorporated herein by reference.

FIELD OF THE INVENTION

This invention relates broadly to a multi-step conversion process for the production and reaction of olefins. The invention more directly relates to the transfer of a dehydrogenation effluent to an etherification zone, the recycle of dehydrogenatable materials from the etherification zone to the dehydrogenation zone, and the separation of light hydrocarbons from the dehydrogenation zone and etherification zone effluents.

BACKGROUND OF THE INVENTION

Processes for producing olefins by the dehydrogenation of saturated hydrocarbons are well known. A typical dehydrogenation process mixes the feed hydrocarbons with hydrogen and heats the resulting admixture by indirect heat exchange with the effluent from the dehydrogenation zone. Following heating, the feed mixture passes through a heater to further increase the temperature of the feed components before it enters the dehydrogenation zone where it is contacted with the dehydrogenation catalyst. The catalyst zone may be operated with a fixed bed, a fluidized bed, or a movable bed of catalyst particles. After heat exchange with the feed, the dehydrogenation zone effluent passes to product separation facilities. The product separation facilities will typically produce a gas stream, made up primarily of hydrogen, a first product stream comprising the desired olefin products, and a second potential product stream comprising light hydrocarbons. The light hydrocarbon stream typically has fewer carbon atoms per molecule than the desired olefin product. Light hydrocarbons are generally removed from the product stream in order to reduce flow volume, operating pressures, and undesirable side reactions or coking in downstream process units that receive the olefin product. A portion of the hydrogen stream is typically recycled to the dehydrogenation zone to provide hydrogen for the combined feed stream. The product stream usually contains unconverted dehydrogenatable feed hydrocarbons in addition to the product olefin. These unconverted hydrocarbons may be withdrawn in the separation facilities for recycle to the dehydrogenation zone or passed together with the product olefins to hydrocarbon conversion processes that use the product olefins.

Dehydrogenated hydrocarbons are used in etherification processes for making high octane compounds which are used as blending components in lead-free gasoline. These etherification processes will usually produce ethers by combination of an isoolefin with a monohydroxy alcohol. The etherification process can also be used as a means to produce pure isoolefins by separation and subsequent cracking of the product ether. For instance, pure isobutylene can be obtained for the manufacture of polyisobutylenes and tert-butylphenol by cracking methyl tertiary butyl ether (MTBE). The production of MTBE has emerged as a predominant etherification process which uses $C_4$ isoolefins as the feedstock. A detailed description of processes, including catalyst, processing conditions, and product recovery, for the production of MTBE from isobutylene and methanol are provided in U.S. Pat. Nos. 2,720,547 and 4,219,678 and in an article at page 35 of the June 25, 1979 edition of Chemical and Engineering News. The preferred process is described in a paper presented at The American Institute of Chemical Engineers, 85th National Meeting on June 4-8, 1978, by F. Obenaus et al. Another etherification process of current interest is the production of tertiary amyl ether (TAME) by reacting $C_5$ isoolefins with methanol.

Due to the limited availability of olefins for olefin conversion processes, such as etherification, it has become common practice to combine a dehydrogenation zone and an olefin conversion process. General representations of flow schemes where a dehydrogenation zone effluent passes to an etherification zone are shown in U.S. Pat. Nos. 4,118,425 4,447,653 and 4,465,870. U.S. Pat. Nos. 4,447,653 and 4,465,870 issued to Vora and Herskovits, respectively, represent the usual arrangement of dehydrogenation and etherification combinations that employ fractionation for deethanization and depropanization between dehydrogenation and etherification facilities. More complete representations of a flow arrangement where the dehydrogenation zone effluent passes to an etherification zone are given in U.S. Pat. No. 4,329,516 and at page 91 of the October, 1980 edition of Hydrocarbon Processing. The latter two references also depict the typical gas compression and separation steps that are used to remove hydrogen and light ends from the dehydrogenation zone effluent before it passes to the etherification zone. A typical effluent from an etherification zone includes an ether product, unreacted alcohol, and unreacted hydrocarbons which include light ends. These effluent components enter separation facilities that yield the ether product, alcohol for recycling to the etherification zone, hydrocarbons for further processing including dehydrogenation, and light ends which can be further separated into fuel and chemical feedstocks.

It is a broad object of this invention to improve the arrangement and operation of a combination process for dehydrogenating hydrocarbons and reacting the dehydrogenated hydrocarbons.

A more specific object of this invention is to simplify the separation facilities in a combined process for the dehydrogenation of dehydrogenatable hydrocarbons and the etherification of the dehydrogenated hydrocarbons.

BRIEF SUMMARY OF THE INVENTION

This invention provides a simplified combination dehydrogenation-etherification process. The process is simplified by the reducing the separation facilities that prepare the dehydrogenation zone effluent for transfer to the etherification zone and the consolidation of separation requirements into a single column located downstream of the etherification zone.

Thus, in a broad embodiment, this invention is a method of preparing ethers from a feed stream comprising $C_4$-$C_5$ isoalkane hydrocarbons. The steps of this process include dehydrogenating the feed stream in a dehydrogenation zone at dehydrogenation conditions including a temperature in the range of 500° C. (930° F.) to 700° C. (1290° F.), a pressure of from 0.1 to 3 bars and in the presence of dehydrogenation catalyst to produce a dehydrogenation effluent comprising isoolefins, isoalkanes, and light gases. Essentially all $C_3$ and higher hydrocarbons from the dehydrogenation effluent are passed to an etherification zone and combined with a $C_1$–$C_5$ alcohol in the etherification zone at etherification conditions to obtain essentially complete conversion of isoolefins and an etherification effluent comprising isoalkanes, alcohol, light gases, and ether. The etherification effluent is separated in a single fractionation column into at least a product stream comprising ether, a recycle stream comprising isoalkanes and a light gas stream comprising the light gases. A product stream, recycle stream and light gas stream are recovered from the column as a bottoms stream, sidecut stream, and overhead stream, respectively.

In a specific aspect, this invention is a method for preparing ethers from a feed stream of isobutane. In this method, the feed stream is combined with a hydrogen stream and an isobutane recycle stream to provide a combined feed. The combined feed is dehydrogenated in a dehydrogenation zone at dehydrogenation conditions which include a temperature in the range of 550° C. (1020° F.) to 750° C. (1380° F.) and a pressure of from 0.1 to 3 bars and in the presence of a dehydrogenation catalyst. A dehydrogenation zone effluent made up of isobutylene, isobutane, and light gases having less than four carbon atoms per molecule emanates from the dehydrogenation zone and enters a dehydrogenation separation section for the recovery of hydrogen for the hydrogen recycle stream. The remainder of the dehydrogenation zone effluent which contains at least all $C_3$ and higher hydrocarbons passes to an etherificatin zone where it is combined with methanol at etherification conditions including a temperature of 35° C. (95° F.) to 100° C. (210° F.), and a pressure of 1 to 70 bars absolute. The etherification zone provides an essentially complete conversion of isobutylene. An etherification zone effluent made up of methyl tertiary butyl ether, isobutane, methanol, and light gases having less than four carbon atoms per molecule is separated in a single column into at least a product stream comprising the methyl tertiary butyl ether, an isobutane recycle stream which is returned to the dehydrogenation zone and a light gas stream containing the light gases.

Additional embodiments, aspects, and details of this invention are set forth in the following detailed description.

BRIEF DESCRIPTION OF THE DRAWING

The drawing schematically shows a combined dehydrogenation and etherification process. This process has four main sections, a dehydrogenation reactor section 10, a dehydrogenation separation section 12, an MTBE reactor section 14, and an MTBE separation section 16.

DETAILED DESCRIPTION OF THE INVENTION

Essential to the operation of this invention is a dehydrogenation zone or reaction section for the production of olefins from dehydrogenatable hydrocarbons. Dehydrogenatable hydrocarbons for this invention include any hydrocarbons having 3 to 5 carbon atoms and saturated carbon bonds which may be unsaturated by the dehydrogenation process. Preferably, the dehydrogenatable hydrocarbons will be paraffins containing from 3 to 5 carbon atoms and the dehydrogenation process will produce monoolefins. Of these hydrocarbons, butane and pentane, especially isobutane and isopentane, are particularly important. A suitable feed of dehydrogenatable hydrocarbons will often contain light hydrocarbons (i.e., those having less carbon atoms than the primary feed components) which, for the purpose of this invention, serve as contaminants. These light hydrocarbons will typically include $C_2$ and $C_3$ hydrocarbons.

Along with the dehydrogenatable hydrocarbons, the feed to the dehydrogenation zone of the present invention comprises an $H_2$ rich stream, preferably containing at least 75 mole percent $H_2$. The presence of $H_2$ within the dehydrogenation zone serves several purposes. First, the $H_2$ acts to suppress the formation of hydrocarbonaceous deposits on the surface of the catalyst, more typically known as coke. Secondly, $H_2$ can act to suppress undesirable thermal cracking. Because $H_2$ is generated in the dehydrogenation reaction and comprises a portion of the effluent, the $H_2$ rich stream introduced into the reaction zone generally comprises recycle $H_2$ derived from separation of the dehydrogenation zone effluent. Alternately, the $H_2$ may be supplied from suitable sources other than the dehydrogenation zone effluent.

The dehydrogenatable hydrocarbon stream and $H_2$ stream are introduced into a dehydrogenation reaction zone. The dehydrogenation reaction zone of this invention preferably comprises at least one radial flow reactor through which the catalytic composite gravitates downwardly to allow a substantially continuous replacement of the catalyst with fresh and/or regenerated catalyst. A detailed description of the moving bed reactors herein contemplated may be obtained by reference to U.S. Pat. No. 3,978,150. The dehydrogenation reaction is a highly endothermic reaction which is typically effected at low (near atmospheric) pressure conditions. The precise dehydrogenation temperature and pressure employed in the dehydrogenation reaction zone will depend on a variety of factors such as the composition of the paraffinic hydrocarbon feedstock, the activity of the selected catalyst, and the hydrocarbon conversion rate. In general, dehydrogenation conditions include a pressure of from about 0 to about 35 bars and a temperature of from about 480° C. (900° F.) to about 760° C. (1400° F.). A suitable hydrocarbon feedstock is charged to the reaction zone and contacted with the catalyst contained therein at a liquid hourly space velocity of from about 1 to about 10. Hydrogen, principally recycle hydrogen, is suitably admixed with the hydrocarbon feedstock in a mole ratio of from about 0.1 to about 10. Preferred dehydrogenation conditions, particularly with respect to $C_4$–$C_5$ paraffinic hydrocarbon feedstocks, include a pressure of from about 0 to about 20 bars and a temperature of from about 540° C. (1000° F.) to about 705° C. (1300° F.), a liquid hourly space velocity of from about 1 to about 5, and a hydrogen/hydrocarbon mole ratio of from about 0.5 to about 2.

The dehydrogenation zone of this invention may use any suitable dehydrogenation catalyst. Generally, the preferred catalyst comprises a platinum group component, an alkali metal component, and a porous inorganic carrier material. The catalyst may also contain promoter metals which advantageously improve the performance of the catalyst. It is preferable that the porous carrier material of the dehydrogenation catalyst be an absorptive high surface area support having a surface area of about 25 to about 500 $m^2/g$. The porous carrier material should be relatively refractory to the conditions utilized in the reaction zone and may be chosen from those carrier materials which have traditionally been utilized in dual function hydrocarbon conversion catalysts. A porous carrier material may, therefore, be chosen from an activated carbon, coke or charcoal, silica or silica gel, clays and silicates including those synthetically prepared and naturally occurring, which may or may not be acid-treated as, for example, attapulgus clay, diatomaceous earth, kieselguhr, bauxite; refractory inorganic oxides such as alumina, titanium dioxide, zirconium dioxides, magnesia, silica alumina, alumina boria, etc.; crystalline alumina silicates such as naturally occurring or synthetically prepared mordenite or a combination of one or more of these materials. The preferred porous carrier material is a refractory inorganic oxide, with the best results being obtained with an alumina carrier material. The aluminas, such as gamma alumina, give the best results in general. The preferred catalyst will have a gamma alumina carrier which is in the form of spherical particles having relatively small diameters on the order of about 1/10 inch.

The preferred dehydrogenation catalyst also contains a platinum group component. Of the platinum group metals, which include palladium, rhodium, ruthenium, osmium and iridium, the use of platinum is preferred. The platinum group component may exist within the final catalyst composite as a compound such as an oxide, sulfide, halide, oxysulfide, etc., or an elemental metal or in combination with one or more other ingredients of the catalyst. It is believed that the best results are obtained when substantially all the platinum group components exist in the elemental state. The platinum group component generally comprises from about 0.01 to about 2 wt. % of the final catalytic composite, calculated on an elemental basis. It is preferred that the platinum content of the catalyst be between about 0.1 and 1 wt. %. The preferred platinum group component is platinum, with palladium being the next preferred metal. The platinum group component may be incorporated into the catalyst composite in any suitable manner such as by coprecipitation or cogelation with the preferred carrier material, or by ion-exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinum or chloropalladic acid. An acid such as hydrogen chloride is generally added to the impregnation solution to aid in the distribution of the platinum group component throughout the carrier material.

Additionally, the preferred catalyst contains an alkali metal component chosen from cesium, rubidium, potassium, sodium, and lithium. The preferred alkali metal is normally either potassium or lithium, depending on the feed hydrocarbon. The concentration of the alkali metal may range from about 0.1 to 5 wt. %, but is preferably between 1 and about 4 wt. % calculated on an elemental basis. This component may be added to the catalyst by the methods described above as a separate step or simultaneously with the solution of another component. With some alkali metals, it may be necessary to limit the halogen content to less than 0.5 wt. % and preferably less than 0.1 wt. %, while others may have higher halogen content.

As noted previously, the dehydrogenation catalyst may also contain promoter metal. One such preferred promoter metal is tin. The tin component should constitute about 0.01 to about 1 wt. % tin. It is preferred that the atomic ratio of tin to platinum be between 1:1 and about 6:1. The tin component may be incorporated into the catalytic composite in any suitable manner known to effectively disperse this component in a very uniform manner throughout the carrier material. Thus, the component may be added to the carrier by coprecipitation.

A preferred method of incorporating the tin component involves coprecipitation during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into an oil bath. The tin component may also be added through the utilization of a soluble decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

Effluent from the dehydrogenation reaction section passes to a dehydrogenation separation section. This separation section removes hydrogen from the effluent and purifies the hydrogen for recycle to the dehydrogenation reaction section. Separation steps for the removal of hydrogen will normally include cooling and compressing with subsequent flashing in a separation vessel. Such methods for the separation of hydrogen and light gases are well known by those skilled in the art. The advantages of this invention can be realized by operating these separation facilities to allow essentially all $C_3$ and higher hydrocarbons to pass through the olefin conversion zone. More typically, these steps will remove primarily hydrogen and methane from the dehydrogenation zone effluent. These separation facilities are preferably designed to reduce the concentration of hydrogen and methane in the effluent to equilibrium amounts. Reduction of hydrogen and methane to equilibrium amounts will allow the olefin conversion zone to operate with only a slight increase in pressure over that required for a more complete removal of light end materials. Remaining light hydrocarbons and undehydrogenated hydrocarbons are passed with the olefins to an olefin conversion zone. Thus, this invention also includes an arrangement where substantial quantities of $C_2$ hydrocarbons are passed from the dehydrogenation zone to an etherification zone. The concentration of $C_2$ hydrocarbons passing to the etherification zone can range from less than 5 wt. % of the $C_2$ hydrocarbons originally present in the dehydrogenation zone effluent to essentially all of the $C_2$ hydrocarbons.

In the etherification zone, olefins are combined with one or more alcohols to obtain a higher boiling compound derived in part from the olefin component. In order to obtain complete conversion, an excess of the alcohol is usually present in the etherification zone. It has been found for the etherification process that the presence of hydrocarbons having fewer carbon atoms than the olefin reactants will not unduly interfere with the operation of the etherification zone. The major changes in the etherification zone resulting from the presence of the additional light materials such as methane, ethane, ethylene, etc. will be an increased pressure and additional throughput. For the etherification operation, these changes are relatively small and do not interfere with the olefin reactions or increase the operational utilities. An important characteristic of the etherification zone is that it converts essentially all of the olefins having a particularly range of carbon numbers to a higher boiling compound.

The preferred conversion zone is an etherification process for the production of MTBE. Several suitable etherification processes have been described in the available literature, with these processes being presently used to produce MTBE. The preferred form of the etherification zone is similar to that described in U.S. Pat. No. 4,219,678 and shown in the previously cited paper. In this instance, the isobutylene or other isoolefin, methanol or other feed alcohol, and a recycle stream containing recovered excess alcohol are passed into the etherification zone and contacted with an acidic catalyst while maintained at etherification conditions.

A wide range of materials are known to be effective as etherification catalysts for the preferred reactants including mineral acids such as sulfuric acid, boron trifluoride, phosphoric acid on kieselguhr, phosphrus-modified zeolites, heteropoly acids, and various sulfonated resins. The use of a sulfonated solid resin catalyst is preferred. These resin type catalysts include the reaction products of phenolformaldehyde resins and sulfuric acid and sulfonated polystyrene resins including those crosslinked with divinylbenzene. Further information on suitable etherification catalysts may be obtained by reference to U.S. Pat. Nos. 2,480,940, 2,922,822, and 4,270,929 and the previously cited etherification references.

A broad range of suitable etherification conditions includes a superatmospheric pressure sufficient to maintain the reactants as a liquid phase, generally below about 200 bars, and a temperature between about 30° C. (85° F.) and about 100° C. (210° F.). Due to the presence of additional light materials, pressures in the range of 10 to 40 bars are preferred. A preferred temperature range is from 50° C. (120° F.) to 100° C. (210° F.). The reaction rate is normally faster at higher temperatures but conversion is more complete at lower temperatures. High conversion in a moderate volume reaction zone can, therefore, be obtained if the initial section of the reaction zone, e.g., the first two-thirds, is maintained above 70° C. (160° F.) and the remainder of the reaction zone is maintained below 50° C. (120° F.). This may be accomplished most easily with two reactors. The ratio of feed alcohol to isoolefin should normally be maintained in the broad range of 1:1 to 2:1. With the preferred reactants, good results are achieved if the ratio of methanol to isobutene is between 1.05:1 and 1.5:1. An excess of methanol above that required to achieve satisfactory conversion at good selectivity should be avoided as some decomposition of methanol to dimethylether may occur.

The effluent from the etherification zone consists of ether, light hydrocarbons, dehydrogenatable hydrocarbons, and any excess alcohol. This effluent passes from the etherification zone to a separation section. The separation section recovers all or a portion of the dehydrogenatable hydrocarbons which are usually recycled back to the dehydrogenation zone. In most cases, olefins are excluded from the dehydrogenation zone recycle in order to avoid the formation of dienes which produce unwanted by-products in many of the olefin conversion processes. Complete conversion of olefins in the etherification zone eliminates olefins that would be otherwise difficult to remove from the dehydrogenation recycle stream. In addition to the dehydrogenatable hydrocarbons, the separation section recovers at least two additional fractions from the etherification zone effluent comprising ether and light hydrocarbons having less carbon atoms per molecule than the reacted olefins. In most cases, the ether product is withdrawn by itself as the heaviest component in the conversion zone effluent. Thus, the separation section can be designed to withdraw the product at a desired degree of purity. Alcohol typically remains in admixture with the recycle and ether stream and may be removed by subsequent separation for recycle to the etherification zone.

The light hydrocarbon fraction normally comprises $C_3$ and lighter hydrocarbons. When the quantity of $C_3$ and higher hydrocarbons is low, the light hydrocarbon fraction is normally cooled and sent to a vapor liquid drum to obtain a liquid reflux for the separation facilities and a fuel gas stream which is withdrawn from the combined process. When sufficient propane/propylene and higher hydrocarbons are present, an additional liquid product stream can be recovered from the light hydrocarbon stream. When separating the dehydrogenatable hydrocarbons the separation facilities normally need not provide a good cut between the light ends and the dehydrogenatable hydrocarbons. This is true whe the dehydrogenatable hydrocarbons are primarily recycled back to the dehydrogenation zone. Since the dehydrogenation zone can normally tolerate these light hydrocarbons, allowing some light hydrocarbons to pass with dehydrogenatable hydrocarbons eases the severity of the separation zone.

Significant cost savings have been achieved in this invention by consolidating the primary separation facilities for the etherification zone into a single fractionation column. The column provides an overhead, sidecut, and bottoms stream comprising the light ends, dehydrogenation recycle, and bottoms stream, respectively. When the column receives the effluent from the etherification zone for the reaction of an isoolefin ad a $C_1$–$C_5$ alcohol, the overhead stream will comprise hydrocarbons lighter than the isoolefin, the sidecut will include isoalkanes having the same number of carbon atoms as the isoolefins and the bottoms stream will comprise an ether.

This invention will be further described in the context of an example for the production of MTBE. The description of this invention in terms of this specific process example is not meant to limit this invention to the particular details disclosed herein. This example is based on engineering calculations and experience with the operation of similar process units. The drawing provides a schematic drawing for this type of operation. The drawing shows only those compressors, heat exchangers, coolers, and separators that are useful in the description of the process. The utilization of other miscellaneous hardware such as heaters, valves, reboilers, pumps, instrumentation, and controls have been omitted as not essential to a clear understanding of the process, the use of such hardware being well within the purview of one skilled in the art.

Referring then to the drawing, a hydrocarbon input stream comprising isobutane is charged to line 18 from a deisobutanizer column which is not shown. The feed stream is combined with a hereinafter described recycle isobutane stream 20 to obtain a dehydrogenation feed stream 22 which passes through a dehydrogenation separation section 12. In separation section 12, the dehydrogenation feed stream is heat exchanged and transported to dehydrogenation reactor section 10 by way of line 24 at a temperature of about 40° C. (100° F.) and at a pressure of about 3 bars (40 psig). In addition to the feed stream, a hereinafter described hydrogen-rich recycle stream from line 26 provides hydrogen to reactor section 10 to obtain a desired hydrogen/hydrocarbon ratio.

Preferably, dehydrogenation reactor section 10 comprises multiple stacked or side by side reaction zones, and a combined stream of hydrogen and hydrocarbon fed is processed serially through said zones each of which contains a particulate catalyst disposed as an annular-form bed movable downwardly through said zones. The combined stream is then processed through said annular-form beds in a substantially radial flow and, since the dehydrogenation reaction is endothermic in nature, intermediate heating of the reactant stream between zones is the preferred practice. The moving catalyst bed permits a continuous addition of fresh and/or regenerated catalyst and the withdrawl of spent catalyst. The moving bed system herein contemplated is illustrated in U.S. Pat. No. 3,647,680 in conjunction with a continuous catalyst regeneration system, and in U.S. Pat. No. 3,978,150 with reference to the dehydrogenation of paraffinic hydrocarbons.

Regardless of the actual reactor details, the hot effluent stream from the dehydrogenation section 10 is recovered through line 28 and has the composition given in the Table. The reactor section effluent stream, at a temperature of about 95° C. (200° F.) and a pressure slightly above atmospheric is passed to dehydrogenation separation section 12. In separation section 12, the dehydrogenation effluent is cooled and compressed, and again cooled to obtain a dried reactor effluent vapor phase stream for further cooling and condensing where it is exchanged against feed stream 22 and finally introduced into one or more separators. The separators yield a liquid hydrocarbon phase and a hydrogen-rich vapor phase which, after heat exchange, exits separation section 12 at a temperature of about 40° C. (100° F.) and a pressure of about 50 psig. A portion of the hydrogen-rich vapor phase, substantially equivalent to the net hydrogen product, is taken from separation section 12 through line 32 and processed for further use. The remainder of the hydrogen-rich vapor stream continues through line 26 and enters dehydrogenation reactor section 10 as previously described. The liquid hydrocarbon phase is pumped from separation section 12 through line 34 at a pressure of about 25 bars and at a temperature of about 65° C. (150° F.). The contents of line 34 have the relative composition given in the Table.

The contents of line 34 enter MTBE reaction section 14 to which methanol is added via line 36 to provide a 1:1 to 1.1:1 ratio of methanol to isobutylene. The added methanol consists of fresh methanol and recycle methanol added via line 38. The combined reactants pass through a sulfonic resin catalyst at temperature of 65° C. (150° F.) and a pressure of 10 to 15 bars (150 to 200 psig). An etherification zone effluent is withdrawn by line 40 and has the composition given in the Table. Line 40 carries the etherification zone effluent to etherification separation section 16 at a temperature of 45° C. (110° F.) and a pressure of 10 to 15 bars.

The etherification separation section 16 includes an ordinary tray-type column 42 of conventional design that receives the contents of line 40 at a tray elevation located at or below the column midpoint and divides the etherification zone effluent into three fractions. The total overhead of line 44 is cooled in exchanger 46 and passed to phase separation drum 48 from which a net overhead product is withdrawn via line 50 and an overhead liquid is withdrawn via line 52. The overhead liquid of line 52 comprising mainly $C_3$-$C_4$ hydrocarbons, is returned to the column as reflux via line 52. In some instances, a liquid product stream may also be taken from line 52. Line 50 contains the lightest fraction which comprises light ends taken overhead at a temperature of 40° C. (100° F.) and a pressure of 10 to 15 bars (150 to 200 psig) through line 50. The net overhead of line 50 has the relative composition given in the Table. Line 58 takes a sidecut fraction, having the composition given in the Table, from the column at a temperature of about 95° C. (200° F.). This stream has a small percentage of $C_3$ and lower hydrocarbons which is permitted to reduce the severity of the cut between the overhead and sidecut stream. Line 58 also withdraws the majority of the unreacted methanol which is separated from the contents of line 58 by oxygenate removal zone and returned to MTBE reaction section via line 38. After removal of oxygenates, the remainder of the sidecut is taken by line 20 for eventual return to the dehydrogenation reaction section. The third fraction, MTBE product, at a purity of 99 plus % leaves the bottom of the column through line 62 and its composition is given in the Table.

What is claimed is:

1. A method of preparing ethers from a feed stream comprising $C_4$-$C_5$ isoalkane hydrocarbons which comprises:
    (a) dehydrogenating said feed stream in a dehydrogenation zone at dehydrogenation conditions including a temperature in the range of 500° C. (930° F.) to 700° C. (1290° F.), a pressure of from 0.1 to 3 bars and in the presence of a dehydrogenation catalyst to produce a dehydrogenation effluent comprising $C_4$-$C_5$ isoolefins and isoalkanes, and light gases, said light gases including hydrocarbons having at least as few as 3 carbon atoms per molecule:
    (b) passing at least all $C_3$ and higher hydrocarbons in said dehydrogenation effluent to an etherification zone;
    (c) combining at least all $C_3$ and higher hydrocarbons and a $C_1$-$C_5$ alcohol in said etherification zone at etherification conditions to obtain essentially complete conversion of said isoolefins and an etherification effluent comprising isoalkanes, alcohol, light gases, and ether;

TABLE

| | Compositions in mol % | | | | | |
|---|---|---|---|---|---|---|
| | Line 28 | Line 34 | Line 40 | Line 50 | Line 58 | Line 62 |
| $H_2$ | 27 | Trace | Trace | 0.4 | — | — |
| $C_1$ | 5 | 2 | 2 | 27.6 | — | — |
| $C_2$ | 1 | 1 | 1 | 13.8 | — | — |
| $C_3$ | 3 | 4 | 4 | 53.2 | 0.3 | — |
| isobutane | 33 | 47 | 47.5 | 5.0 | 92.0 | Trace |
| isobutene | 30 | 43 | 1 | — | 1.9 | — |
| Other $C_4'$ | 1 | 2 | 2 | — | 3.9 | — |
| $C_5$ & heavier hydrocarbons | — | — | — | — | — | 0.7 |
| MEOH | — | — | 1 | — | 1.9 | Trace |
| MTBE | — | — | 41.5 | — | — | 99.3 |
| | 100 | 100 | 100 | 100 | 100 | 100 |

(d) separating said etherification effluent into at least a product stream comprising ether, a recycle stream comprising isoalkanes and a light gas stream comprising said light gases in a single fractionation column and recovering said product stream, recycle stream, and light gas stream from said column as a bottoms stream, sidecut stream, and an overhead stream, respectively; and (e) returning at least a portion of said recycle stream to said dehydrogenation zone.

2. The method of claim 1 wherein said dehydrogenation zone effluent includes hydrogen, hydrogen is recovered from said dehydrogenation zone effluent and at least a portion of said hydrogen is admixed with said feed stream.

3. The method of claim 1 wherein said dehydrogenation zone effluent includes hydrogen, methane and $C_2$ hydrocarbons, hydrogen and methane are separated from said dehydrogenation effluent and essentially all $C_2$ and higher hydrocarbons from said dehydrogenation effluent are passed to said etherification zone.

4. The process of claim 1 wherein said sidecut stream contains unreacted alcohol from said etherification effluent and at least a portion of said unreacted alcohol from said sidecut stream is recovered and recycled to said etherification zone.

5. A method of preparing ethers from a feed stream comprising $C_4$–$C_5$ isoalkane hydrocarbons which comprises:

(a) dehydrogenating said feed stream in a dehydrogenation zone at dehydrogenation conditions including a temperature in the range of 500° C. (930° F.) to 700° C. (1290° F.), a pressure of from 0.1 to 3 bars and in the presence of a dehydrogenation catalyst to produce a dehydrogenation effluent comprising $C_4$–$C_5$ isoolefins and isoalkanes and light gases, said light gases including hydrocarbons having at least as few as 2 carbon atoms per molecule;

(b) passing $C_2$ hydrocarbons and essentially all $C_3$ and higher hydrocarbons in said dehydrogenation effluent to an etherification zone;

(c) combining $C_2$ hydrocarbons and essentially all $C_3$ and higher hydrocarbons and a $C_1$–$C_5$ alcohol in said etherification zone at etherification conditions to obtain essentially complete conversion of said isoolefin and an etherification effluent comprising isoalkanes, alcohol, light gases, and ether;

(d) separating said etherification effluent into at least a product stream comprising ether, a recycle stream comprising isoalkanes and a light gas stream comprising said light gases in a single fractionation column and recovering said product stream, recycle stream, and light gas stream from said column as a bottoms stream, sidecut stream, and overhead stream, respectively; and (e) returning at least a portion of said recycle stream to said dehydrogenation unit.

6. The process of claim 5 wherein said dehydrogenation zone effluent includes hydrogen, hydrogen is recovered from said dehydrogenation effluent at least a portion of hydrogen is admixed with said feed.

7. The process of claim 5 wherein essentially all $C_2$ and higher hydrocarbons from said dehydrogenation effluent are passed to said etherification zone.

8. A method for preparing ethers from a feed stream comprising isobutane which comprises:

(a) combining said feed stream with a hydrogen stream and an isobutane recycle stream to obtain a combined feed stream;

(b) passing said combined feed stream to a dehydrogenation zone and dehydrogenating said combined feed stream in said dehydrogenation zone at dehydrogenation conditions including a temperature in the range of 500° C. (930° F.) to 700° C. (1290° F.), a pressure of from 0.1 to 3 bars and in the presence of a dehydrogenation catalyst to obtain a dehydrogenation effluent comprising isobutene, isobutane, and light gases, said light gases including hydrocarbons having at least as few as 2 carbon atoms per molecule;

(c) removing hydrogen from said dehydrogenation zone effluent and recovering at least a portion of said hydrogen in said hydrogen stream;

(d) passing essentially all $C_2$ and higher hydrocarbons in said dehydrogenation effluent to an etherification zone;

(e) combining said essentially all $C_2$ and higher hydrocarbons and a $C_1$–$C_5$ alcohol in said etherification zone at etherification conditions including a temperature of 50° C. (120° F.) to 80° C. (175° F.), a pressure of 10 bars to 15 bars and in the presence of an etherification catalyst to obtain essentialy complete conversion of isobutene and produce an etherification effluent stream comprising a tertiary butyl ether, isobutane, alcohol, and light gases having less than 4 carbon atoms per molecule; and (f) separating said etherification effluent into at least a product stream comprising ether, said isobutane recycle stream, and a light gas stream comprising said light gases in a single fractionation column and recovering said product stream, recycle stream, and light gas stream from said column as a bottoms stream, sidecut stream, and overhead stream, respectively.

9. The method of claim 8 wherein said dehydrogenation catalyst comprises Pt on alumina and said etherification catalyst is a sulfonic acid resin.

10. The process of claim 9 wherein said $C_1$–$C_5$ alcohol consists of methanol and said etherification zone produces MTBE.

11. The process of claim 10 wherein said sidecut stream contains unreacted methanol, said sidecut stream is further processed to recover unreacted methanol, and at least a portion of said methanol is returned to said etherification zone.

* * * * *